United States Patent
Kuroda et al.

(10) Patent No.: US 6,172,243 B1
(45) Date of Patent: Jan. 9, 2001

(54) PROCESS FOR PRODUCING EPOXYCYCLODODECADIENE

(75) Inventors: Nobuyuki Kuroda; Mitsuo Yamanaka; Hirofumi Takemoto; Kohei Ninomiya; Junichi Kugimoto, all of Yamaguchi (JP)

(73) Assignee: Ube Industries, Ltd., Yamaguchi Prefecture (JP)

( * ) Notice: Under 35 U.S.C. 154(b), the term of this patent shall be extended for 0 days.

(21) Appl. No.: 09/523,392

(22) Filed: Mar. 10, 2000

(30) Foreign Application Priority Data

Mar. 12, 1999 (JP) .................................................. 11-065916
Jun. 25, 1999 (JP) .................................................. 11-180082

(51) Int. Cl.$^7$ .................................................. C07D 301/12

(52) U.S. Cl. .............................................................. 549/531

(58) Field of Search ............................................. 549/531

(56) References Cited

U.S. PATENT DOCUMENTS 4,882,442 * 11/1989 Edl et al. ................................ 549/525
6,043,383 * 3/2000 Kuroda et al. ........................ 549/513

FOREIGN PATENT DOCUMENTS 38-722      3/1959  (JP) .
56-104877   8/1981  (JP) .

* cited by examiner

*Primary Examiner*—Ba K. Trinh
(74) *Attorney, Agent, or Firm*—Akin, Gump, Strauss, Hauer & Feld, L.L.P.

(57) ABSTRACT

Described is a process for producing 1,2-epoxy-5,9-cyclododecadiene, which comprises bringing 1,5,9-cyclododecatriene into contact with hydrogen peroxide in the presence of a carboxylic acid having an acid dissociation constant K at 25° C. of $5.0 \times 10^{-6} \leq K \leq 1.0 \times 10^{-4}$. The present invention makes it possible to provide an industrially desirable process which permits the production of 1,2-epoxy-5,9-cyclododecadiene with good selectivity and facilitates control of reaction including shortening of the reaction time.

9 Claims, No Drawings

PROCESS FOR PRODUCING EPOXYCYCLODODECADIENE

BACKGROUND OF THE INVENTION

1. Field of the Invention

This invention relates a process for producing 1,2-epoxy-5,9-cyclododecadiene by bringing 1,5,9-cyclododecatriene into contact with hydrogen peroxide. Not only 1,2-epoxy-5,9-cyclododecadiene can be used as a resin component of a coating composition, an adhesive or the like because of having an active epoxy group and a carbon-carbon unsaturated bond, but also it is an important compound as an intermediate raw material for synthetic fibers or synthetic resins such as polyamide or polyester because it can easily be introduced, after conversion into cyclododecanone, into the corresponding lactam, lactone or dibasic acid in a known manner.

2. Description of the Related Art

As a process for producing 1,2-epoxy-5,9-cyclododecadiene by bringing 1,5,9-cyclododecatriene into contact with hydrogen peroxide in the presence of an aliphatic carboxylic acid, conventionally known is a process (Japanese Patent Publication JP-B-38-772, Unexamined published Japanese Patent Application JP-A-56-104877) in which formic acid and/or halogenoacetic acid is used in a catalytic amount relative to hydrogen peroxide. As a result of the follow-up test of the above-described invention, the present inventors have found that the process is accompanied with such drawbacks as markedly low selectivity to 1,2-epoxy-5,9-cyclododecadiene based on the consumption amount of hydrogen peroxide and necessity of long hours for completion of the reaction.

SUMMARY OF THE INVENTION

An object of the present invention is to provide an industrially desirable process for producing 1,2-epoxy-5,9-cyclododecadiene by bringing 1,5,9-cyclododecatriene into contact with hydrogen peroxide, which process permits production of 1,2-epoxy-5,9-cyclododecadiene with good-selectivity and facilitates control of reaction including shortening of reaction time.

The object of the present invention is attained by a process for producing 1,2-epoxy-5,9-cyclododecadiene by bringing 1,5,9-cyclododecatriene into contact with hydrogen peroxide in the presence of a carboxylic acid having an acid dissociation constant K at 25° C. of $5.0 \times 10^{-6} \leq K \leq 1.0 \times 10^{-4}$.

DETAILED DESCRIPTION OF THE INVENTION

The present invention will hereinafter be described more specifically.

Examples of the carboxylic acid usable in the reaction of the present invention include aliphatic carboxylic acids, alicyclic carboxylic acids and aromatic carboxylic acids each having an acid dissociation constant K at 25° C. of $5.0 \times 10^{-6} \leq K \leq 1.0 \times 10^{-4}$, of which the aliphatic carboxylic acids, alicyclic carboxylic acids and aromatic carboxylic acids each having 2 to 8 carbon atoms and an acid dissociation constant K at 25° C. of $5.0 \times 10^{-6} \leq K \leq 1.0 \times 10^{-4}$ are preferred.

Use of carboxylic acids having an acid dissociation constant K greater than $1.0 \times 10^{-4}$ deteriorates the selectivity to 1,2-epoxy-5,9-cyclododecadiene, the target product. When those having an acid dissociation constant K less than $5.0 \times 10^{-6}$ are used, on the other hand, a reaction-rate lowering tendency is recognized.

Specific examples include, among the compounds described in Kagaku Binran Kiso-hen (*Chemistry Handbook, Basic Course*), 4th Edition, II-317 to II-321, published on Sep. 30, 1993 by Maruzen Co., Ltd., linear or branched aliphatic carboxylic acids such as acetic acid, propionic acid, butyric acid, isobutyric acid, valeric acid, isovaleric acid, pivalic acid, hexanoic acid, heptanoic acid and octanoic acid, alicyclic carboxylic acids such as cyclohexylcarboxylic acid and aromatic carboxylic acids such as benzoic acid. Preferred are acetic acid and propionic acid. These carboxylic acids may be used either singly or in combination.

Although the carboxylic acid can be added in an amount of at least 0.5 mole per mole of the charged amount of hydrogen peroxide without any particular problem in the reaction of the present invention, an amount of 1 to 50 moles is preferred, with an amount of 2 to 30 moles being more preferred. When the carboxylic acid is added in an amount less than 0.5 mole, it takes a long period of time to complete the reaction and at the same time, a lowering tendency of the selectivity to the target product is recognized. An excessively large amount is, on the other hand, not economical, because it takes much energy to separate the carboxylic acid.

Although there is no limitation imposed on the concentration of hydrogen peroxide to be used in the reaction of the present invention, a 10 to 70 wt. % aqueous solution is preferred in consideration of handling safety and economy. It is used in an amount of 0.05 to 1.2 moles, preferably 0.1 to 1.0 mole, more preferably 0.25 to 1.0 mole per mole of 1,5,9-cyclododecatriene.

As 1,5,9-cyclododecatriene to be used in the present invention, a commercially available one can be used as it is or after purified once.

In the present invention, the reaction proceeds no matter whether the mixture upon reaction is a homogeneous system or a heterogeneous system, but the former is preferred.

The term "homogeneous system" means a system wherein the catalyst, reaction substrate and reaction mixture are not separated into two phases during reaction, which however largely depends on the reaction temperature.

In the reaction according to the present invention, the water content in hydrogen peroxide to be used or water content produced by epoxidizing reaction has a large influence on the results of the reaction, that is, selectivity, reaction rate and operability of reaction. It is preferred to remove, during reaction, water in the reaction system as much as possible in order to make the reaction system homogeneous. More specifically, the reaction system adjusted to have a water content of 20 wt. % or less, preferably 15 wt. % or less, more preferably 10 wt. % or less based on the total weight of the reaction system is preferred.

An excessively large amount of water in the reaction system deteriorates the selectivity to 1,2-epoxy-5,9-cyclododecadiene, the target product.

There is no particular limitation imposed on the method for removing the water content during reaction. Examples include the method to remove the water content by circulating an inert gas with water being adsorbed thereto and the method to separate out water by azeotropy with an ester compound such as ethyl propionate or an aromatic hydrocarbon such as benzene or toluene.

Alternatively, an organic solvent can be used to obtain a homogeneous reaction system. No particular limitation is imposed on the organic solvent insofar as it doesn't inhibit the reaction. Examples include ether compounds such as diethyl ether and dioxane and aliphatic carboxylates such as ethyl acetate and ethyl propionate. These solvents may be used either singly or in combination. The solvent is preferably used in an mount of 0 to 5 times the weight, more preferably 0 to 3 times the weight of 1,5,9-cyclododecatriene.

There is no particular limitation imposed on the reaction of the present invention insofar as it is effected under conditions capable of keeping the homogeneous reaction system during reaction. The reaction is conducted, for example, by mixing 1,5,9-cyclododecatriene, hydrogen peroxide and an aliphatic carboxylic acid in an inert gas atmosphere at normal pressure or under pressure and a reaction temperature of, preferably, 20 to 150° C., more preferably 50 to 130° C. The reaction mixture thus obtained can be isolated or purified by the ordinary method such as distillation.

When, upon conducting the reaction of the present invention, there is a fear of a metal ion or a strong acid, which accelerates decomposition of hydrogen peroxide or ring opening of the epoxy ring of the target product (1,2-epoxy-5,9-cyclododecadiene), being mixed in the reaction system, it is preferred to add a chelating agent such as ethylenediaminetetraacetic acid, a phosphate salt such as sodium pyrophosphate or sodium monohydrogenphosphate, a phosphate ester such as diethylhexyl phosphate, an inorganic base such as sodium carbonate or an organic base such as picolinic acid.

The present invention will hereinafter be described in detail by examples and comparative examples.

EXAMPLE 1

In a glass-made flask having an internal volume of 50 ml and being equipped with a reflux condenser, a nitrogen inlet tube and a thermometer, 9.72 g (60 mmol) of 1,5,9-cyclododecatriene, 0.85 g (15 mmol) of a 60 wt. % aqueous hydrogen peroxide solution and 9.90 g (165 mmol) of acetic acid having an acid dissociation constant K of $2.66 \times 10^{-5}$ were charged (the molar ratio of acetic acid to hydrogen peroxide was 11 at that time), followed by stirring under heat at 90° C. for 1 hour in a nitrogen atmosphere. Under those reaction conditions, the reaction mixture was homogeneous. After completion of the reaction, the reaction mixture was cooled to room temperature and the reaction mixture thus obtained was analyzed.

The remaining hydrogen peroxide, and both of the remaining 1,5,9-cyclododecatriene (which will hereinafter abbreviated as "CDT") and 1,2-epoxy-5,9-cyclododecadiene thus formed (which will hereinafter be called "monoepoxide") were analyzed by iodometry and gas chromatography, respectively. As a result, it was found that the conversion ratio of hydrogen peroxide was 95.8%, the CDT conversion ratio was 24.4% and the monoepoxide -selectivity based on the consumed hydrogen peroxide was 98.5 mol %.

EXAMPLES 2 AND 3

In a similar manner to Example 1, epoxidation was conducted using the composition and reaction conditions shown in Table 1. Under those reaction conditions, the reaction system was homogeneous during the reaction. The results are shown in Table 1.

EXAMPLE 4

In a glass-made flask having an internal volume of 50 ml and being equipped with a reflux condenser, a nitrogen inlet tube and a thermometer, 9.72 g (60 mmol) of 1,5,9-cyclododecatriene, 0.85 g (15 mmol) of a 60 wt. % aqueous hydrogen peroxide solution and 12.2 g (165 mmol) of propionic acid having an acid dissociation constant K of $2.14 \times 10^{-5}$ were charged (the molar ratio of propionic acid to hydrogen peroxide was 11 at that time), followed by stirring under heat at 90° C. for 1 hour in a nitrogen atmosphere. Under those reaction conditions, the reaction mixture was homogeneous. After completion of the reaction, the reaction mixture was cooled to room temperature and the reaction mixture thus obtained was analyzed.

As a result, it was found that the conversion ratio of hydrogen peroxide was 94.1%, the CDT conversion ratio was 23.9% and the monoepoxide selectivity based on the consumed hydrogen peroxide was 98.6 mol %.

EXAMPLES 5 AND 6

In a similar manner to Example 4, epoxidation was conducted using the composition and reaction conditions shown in Table 1. Under those reaction conditions, the reaction system was homogeneous during reaction. The results are shown in Table 1.

EXAMPLE 7

In a glass-made flask having an internal volume of 50 ml and being equipped with a reflux condenser, a nitrogen inlet tube and a thermometer, 9.72 g (60 mmol) of 1,5,9-cyclododecatriene, 0.85 g (15 mmol) of a 60 wt. % aqueous hydrogen peroxide solution and 16.8 g (165 mmol) of pivalic acid having an acid dissociation constant K of $9.33 \times 10^{-6}$ were charged (the molar ratio of pivalic acid to hydrogen peroxide was 11 at that time), followed by stirring under heat at 90° C. for 1 hour in a nitrogen atmosphere. Under those reaction conditions, the reaction mixture was homogeneous. After completion of the reaction, the reaction mixture was cooled to room temperature and the reaction mixture thus obtained was analyzed.

As a result, it was found that the conversion ratio of hydrogen peroxide was 83.7%, the CDT conversion ratio was 21.0% and the monoepoxide selectivity based on the consumed hydrogen peroxide was 98.8 mol %.

COMPARATIVE EXAMPLES 1 AND 2

In Comparative Examples 1 and 2, in a similar manner to Example 1 except that formic acid having an acid dissociation constant of $1.74 \times 10^{-4}$ and monochloroacetic acid having an acid dissociation constant of $1.36 \times 10^{-3}$ were used instead of acetic acid, respectively, epoxidation was conducted. The results are shown in Table 1.

TABLE 1

| Ex. No. | Carboxylic acid (acid dissociation constant at 25° C.) | Carboxylic acid/$H_2O_2$ molar ratio | CDT/$H_2O_2$ molar ratio | Reaction temperature (° C.) | Reaction time (min) | $H_2O_2$ conversion ratio (%) | CDT conversion ratio (%) | Monoepoxide selectivity based on consumed $H_2O_2$ (mol %) |
|---|---|---|---|---|---|---|---|---|
| Ex. 1 | Acetic acid ($2.66 \times 10^{-5}$) | 11 | 4 | 90 | 60 | 95.8 | 24.4 | 98.5 |
| Ex. 2 | Acetic acid ($2.66 \times 10^{-5}$) | 11 | 4 | 100 | 60 | 98.8 | 26.2 | 97.1 |
| Ex. 3 | Acetic acid ($2.66 \times 10^{-5}$) | 11 | 4 | 80 | 120 | 96.8 | 24.6 | 98.4 |
| Ex. 4 | Propionic acid ($2.14 \times 10^{-5}$) | 11 | 4 | 90 | 60 | 94.1 | 23.9 | 98.6 |
| Ex. 5 | Propionic acid ($2.14 \times 10^{-5}$) | 2.5 | 4 | 105 | 60 | 97.8 | 23.7 | 96.1 |
| Ex. 6 | Propionic acid ($2.14 \times 10^{-5}$) | 0.9 | 4 | 105 | 60 | 96.9 | 22.4 | 86.9 |
| Ex. 7 | Pivalic acid ($9.33 \times 10^{-6}$) | 11 | 4 | 90 | 60 | 83.7 | 21.0 | 98.8 |
| Comp. Ex. 1 | Formic acid ($1.74 \times 10^{-4}$) | 11 | 4 | 90 | 60 | 99.7 | 24.8 | 2.0 |
| Comp. Ex. 2 | Monochloro- acetic acid ($1.36 \times 10^{-3}$) | 11 | 4 | 90 | 30 | 95.3 | 25.8 | 11.1 |

EXAMPLE 8

In a glass-made flask having an internal volume of 300 ml and being equipped with a reflux condenser, a nitrogen inlet tube and a thermometer, 47.9 g (300 mmol) of 1,5,9-cyclododecatriene, 4.2 g (75 mmol) of a 60 wt. % aqueous hydrogen peroxide solution and 47.9 g (647 mmol) of 10 propionic acid having an acid dissociation constant K of $2.14 \times 10^{-5}$ were charged (the molar ratio of propionic acid to hydrogen peroxide was 8.6 at that time), followed by stirring under heat at 80° C. for 1 hour in a nitrogen atmosphere. Under those reaction conditions, the reaction mixture was homogeneous. After completion of the reaction, the reaction mixture was cooled to room temperature and the reaction mixture thus obtained was analyzed.

As a result, it was found that the conversion ratio of hydrogen peroxide was 86.2%, the CDT conversion ratio was 22.1% and the monoepoxide selectivity based on the consumed hydrogen peroxide was 93.8 mol %.

EXAMPLES 9 TO 11

In a similar manner to Example 8, epoxidation was conducted using the composition and reaction conditions shown in Table 2. Under those reaction conditions, the reaction system was homogeneous during the reaction. The results are shown in Table 2.

EXAMPLE 12

In a glass-made flask having an internal volume of 300 -ml and being equipped with a reflux condenser, a nitrogen inlet tube and a thermometer, 42.6 g (263 mmol) of 1,5,9-cyclododecatriene, 14.8 g (261 mmol) of a 60 wt. % aqueous hydrogen peroxide solution and 42.6 g (576 mmol) of propionic acid having an acid dissociation constant K of $2.14 \times 10^{-5}$ were charged (the molar ratio of propionic acid to hydrogen peroxide was 2.2 at that time), followed by stirring under heat at 90° C. for 1 hour in a nitrogen atmosphere. Under those reaction conditions, the reaction mixture had been separated into two phases at the initial stage of the reaction, but became homogeneous as the reaction proceeded. After completion of the reaction, the reaction mixture was cooled to room temperature and the reaction mixture thus obtained was analyzed.

As a result, it was found that the conversion ratio of hydrogen peroxide was 73.0%, the CDT conversion ratio was 64.3% and the monoepoxide selectivity based on the consumed hydrogen peroxide was 67.5 mol %. The results are collectively shown in Table 2.

EXAMPLES 13 AND 14

In a similar manner to Example 12, epoxidation was conducted using the composition and reaction conditions shown in Table 2. Also under those reaction conditions, the reaction system had been separated into two phases at the initial stage of the reaction but became homogeneous as the reaction proceeded. The results are collectively shown in Table 2.

TABLE 2

| Ex. No. | Carboxylic acid (acid dissociation constant at 25° C.) | Carboxylic acid/$H_2O_2$ molar ratio | CDT/$H_2O_2$ molar ratio | Reaction temperature (° C.) | Reaction time (min) | $H_2O_2$ conversion ratio (%) | CDT conversion ratio (%) | Monoepoxide selectivity based on consumed $H_2O_2$ (mol %) |
|---|---|---|---|---|---|---|---|---|
| Ex. 8 | Propionic acid ($2.14 \times 10^{-5}$) | 8.6 | 4 | 80 | 60 | 86.2 | 22.1 | 93.8 |
| Ex. 9 | Propionic acid ($2.14 \times 10^{-5}$) | 8.7 | 4 | 90 | 60 | 95.3 | 24.0 | 97.9 |
| Ex. 10 | Propionic acid ($2.14 \times 10^{-5}$) | 6.6 | 3 | 90 | 60 | 93.4 | 31.3 | 95.9 |
| Ex. 11 | Propionic acid ($2.14 \times 10^{-5}$) | 4.4 | 2 | 90 | 60 | 88.0 | 42.6 | 92.2 |
| Ex. 12 | Propionic acid ($2.14 \times 10^{-5}$) | 2.2 | 1 | 90 | 60 | 73.0 | 64.3 | 67.5 |
| Ex. 13 | Propionic acid ($2.14 \times 10^{-5}$) | 4.4 | 1 | 90 | 60 | 81.6 | 72.9 | 69.6 |
| Ex. 14 | Propionic ($2.14 \times 10^{-5}$) | 2.2 | 1 | 90 | 300 | 97 | 79.3 | 61.3 |

EXAMPLE 15

In a glass-made flask having an internal volume of 50 ml and being equipped with a water separator, a reflux condenser, a nitrogen inlet tube and a thermometer, 9.72 g (60 mmol) of 1,5,9-cyclododecatriene, 1.46 g (15 mmol) of a 35 wt. % aqueous hydrogen peroxide solution and 7.0 g (95 mmol) of propionic acid having an acid dissociation constant K of $2.14 \times 10^{-5}$ were charged (the molar ratio of propionic acid to hydrogen peroxide was 6.3 at that time), followed by the addition of 3.0 g of ethyl propionate. The resulting mixture was stirred under heat at 97 to 116° C. for 30 minutes in a nitrogen atmosphere, while water exiting in the reaction system was subjected to azeotropy with ethyl propionate and the resulting distilled water was collected in the water separator filled with ethyl propionate. After completion of the reaction, the reaction mixture was cooled to room temperature and the reaction mixture thus obtained was analyzed. As a result, it was found that the conversion ratio of hydrogen peroxide was 98.6%, the CDT conversion ratio was 24.1% and the monoepoxide selectivity based on the consumed hydrogen peroxide was 97.1 mol %.

The present invention makes it possible to provide an industrially desirable process for producing 1,2-epoxy-5,9-cyclododecadiene with good selectivity, which process comprises bringing 1,5,9-cyclododecatriene into contact with hydrogen peroxide.

What is claimed is:

1. A process for producing 1,2-epoxy-5,9-cyclododecadiene, which comprises bringing 1,5,9-cyclododecatriene into contact with hydrogen peroxide in the presence of a carboxylic acid having an acid dissociation constant K at 25° C. of $5.0 \times 10^{-6} \leq K \leq 1.0 \times 10^{-4}$.

2. The process according to claim 1, wherein the carboxylic acid has 2 to 8 carbon atoms.

3. The process according to claim 1, wherein the carboxylic acid is acetic acid or propionic acid.

4. The process according to claim 1, wherein the carboxylic acid is used in an amount of 1 to 50 moles per mole of hydrogen peroxide.

5. The process according to claim 1, wherein the carboxylic acid is used in an amount of 2 to 30 moles per mole of hydrogen peroxide.

6. The process according to claim 1, wherein hydrogen peroxide is used in an amount 0.05 to 1.2 moles per mole of 1,5,9-cyclododecatriene.

7. The process according to claim 1, wherein hydrogen peroxide is used in an amount 0.1 to 1.0 mole per mole of 1,5,9-cyclododecatriene.

8. The process according to claim 1, wherein hydrogen peroxide is used in an amount 0.25 to 1.0 mole per mole of 1,5,9-cyclododecatriene.

9. The process according to claim 1, wherein the reaction of 1,5,9-cyclododecatriene with hydrogen peroxide is conducted under a homogenous reaction system.

* * * * *